United States Patent
Jennings

(10) Patent No.: US 11,730,747 B2
(45) Date of Patent: Aug. 22, 2023

(54) DRINK PRODUCT AND USE THEREOF

(71) Applicant: HYGIA PHARMACEUTICALS, LLC, Jupiter, FL (US)

(72) Inventor: Barbara Brooke Jennings, Juno Beach, FL (US)

(73) Assignee: HYGIA PHARMACEUTICALS, LLC, Jupiter, FL (US)

( * ) Notice: Subject to any disclaimer, the term of this patent is extended or adjusted under 35 U.S.C. 154(b) by 0 days.

(21) Appl. No.: 17/170,734

(22) Filed: Feb. 8, 2021

(65) Prior Publication Data

US 2021/0369745 A1  Dec. 2, 2021

Related U.S. Application Data

(63) Continuation of application No. 14/775,621, filed as application No. PCT/US2014/023251 on Mar. 11, 2014, now abandoned, and a continuation of application No. 13/972,274, filed on Aug. 21, 2013, now abandoned, which is a continuation-in-part of application No. 13/803,716, filed on Mar. 14, 2013, now abandoned.

(51) Int. Cl.

| | | |
|---|---|---|
| A61K 31/6615 | (2006.01) |
| A61K 9/00 | (2006.01) |
| A61K 31/352 | (2006.01) |
| A61K 45/06 | (2006.01) |
| A61K 47/22 | (2006.01) |
| A61K 47/12 | (2006.01) |
| A61K 47/26 | (2006.01) |
| A23L 33/00 | (2016.01) |
| A23L 2/52 | (2006.01) |
| A61K 31/047 | (2006.01) |
| A61K 31/09 | (2006.01) |
| A61K 31/661 | (2006.01) |

(52) U.S. Cl.
CPC ............ *A61K 31/6615* (2013.01); *A23L 2/52* (2013.01); *A23L 33/40* (2016.08); *A61K 9/0095* (2013.01); *A61K 31/047* (2013.01); *A61K 31/09* (2013.01); *A61K 31/352* (2013.01); *A61K 31/661* (2013.01); *A61K 45/06* (2013.01); *A61K 47/12* (2013.01); *A61K 47/22* (2013.01); *A61K 47/26* (2013.01); *A23V 2002/00* (2013.01)

(58) Field of Classification Search
CPC .. A61K 2300/00; A61K 31/047; A61K 31/09; A61K 31/352; A61K 31/661; A61K 31/6615; A61K 45/06; A61K 47/12; A61K 47/22; A61K 47/26; A61K 9/0095; A61P 39/06; A23L 2/52; A23L 33/40
See application file for complete search history.

(56) References Cited

U.S. PATENT DOCUMENTS

| | | | |
|---|---|---|---|
| 6,417,233 B1 * | 7/2002 | Sears | A61P 21/00 514/689 |
| 6,455,072 B1 * | 9/2002 | Peters | A23L 33/105 424/94.1 |
| 2008/0213401 A1 * | 9/2008 | Smith | A23L 33/10 424/722 |
| 2009/0214474 A1 | 8/2009 | Jennings | |
| 2010/0204204 A1 * | 8/2010 | Zaworotko | A61K 31/522 514/474 |
| 2011/0105433 A1 * | 5/2011 | Braun | A61P 43/00 426/601 |

FOREIGN PATENT DOCUMENTS

| | | |
|---|---|---|
| CN | 1370074 A | 9/2002 |
| CN | 1635907 A | 7/2005 |
| CN | 101128209 A | 2/2008 |
| CN | 101578042 A | 11/2009 |
| WO | 2011064559 A2 | 6/2011 |

OTHER PUBLICATIONS

Notification of the First Office Action dated Jun. 20, 2022 in Chinese Patent Application No. 2021104910326, Issue No. 2022061502514910.

* cited by examiner

*Primary Examiner* — Umamaheswari Ramachandran
(74) *Attorney, Agent, or Firm* — Arentfox Schiff LLP

(57) ABSTRACT

A drink product having pharmaceutical compositions as an active ingredients of, at least one phosphorylated inositol, optionally Genistein, optionally Ubiquinol, and optionally additional unphosphorylated inositol. Uses for prevention, treatment, and reduction in risk of developing or progression of a number of conditions are disclosed.

18 Claims, No Drawings

DRINK PRODUCT AND USE THEREOF

This application is a continuation-in-part of U.S. Ser. No. 13/803,716, filed Mar. 14, 2013 and a continuation-in-part of U.S. Ser. No. 13/972,274, filed Aug. 21, 2013, the priority of both of which is hereby claimed and the entirety of these prior applications in expressly incorporated herein by reference.

FIELD OF THE INVENTION

This invention relates to certain drink products that generally are aqueous solutions containing Genistein (optionally), at least one phosphorylated myoinositol having 1 to 9 phosphate groups (and/or any of the optical isomers thereof) optionally enriched with any or all of myoinositol, optical isomers of myoinositol, electrolytes, flavors, vitamins, free radical scavengers, and sweeteners. The invention further relates to (a) the treatment of and/or (b) the prevention of and/or (c) the reduction in the risk of developing various conditions such as cancers, particularly, lung, skin, prostate, and colon cancers and/or the prevention, and/or (d) reducing the risk of developing HIV and/or AIDS and secondary cancers related to HIV and AIDS and/or (e) prevention HIV infection of resting CD4 T-cells, viral DNA synthesis, and viral nuclear migration. The invention further relates to the inhibition of HIV-1 in a T cell line, the prevention and/or inhibition of the early replicative stage of HIV. Still further, the invention relates to superior cocktails for use in HIV/AIDS treatment, prophylactic treatment in subjects in need of such prophylactic treatment due to either low level detection of HIV/AIDS titers or surrogates therefor or due to suspected exposure to HIV/AIDS virus prior to detection of HIV/AIDS titers or surrogates thereof.

BACKGROUND OF THE INVENTION

A significant statistic has recently shown that a person born in the United States today has a 41% lifetime risk of being diagnosed with some type of cancer. There are approximately, 3.4 million are currently living with HIV/AIDS. Indeed these are alarming statistics. It is so alarming that many health organizations have urged researchers to identify effective methods to prevent cancer and the spread of HIV infections to full blown AIDS. Both cancer cells and viruses exhibit deregulations in multiple cellular signaling pathways. Viruses and cancers are similar in that they both use social networking for survival. Normal cells are compliant to internal environmental cues. On the other hand, cancer cells and virus particles side-step these chemical and physical cues in order to survive and evade the immune system. Some would even report that certain viruses are responsible for various types of cancer such as Burkitt's lymphoma & Hodgkin's lymphoma (Epstein Barr), AIDS (T-cell leukemia), liver cancer (Hepatitis), cervical cancer (HPV). Furthermore, all cancers and HIV infected cells share a number of common hallmark capabilities, such as: Genetic instability, self-sufficiency in growth signals, insensitivity to drugs, avoidance of apoptosis, unlimited replication, sustained internal cellular compartment invasion, metastasis and/or malignancies Therefore, it would be ideal to utilize specific agents that can both target multiple signaling pathways and or proteins. Compounds that can only target a single pathway or a protein in cancer as well as in HIV infections are tactics that frequently fail. Genetic instability produces intra-tumoral heterogeneity and viral heterogeneity (viral mutant) that frequently enables adaptive resistance or drug resistance overtime. Indeed, current combination chemotherapy that targets a number of distinct molecular mechanisms in both cancer and in HIV infections is preferable and considered more promising, but the we of multiple agents known in art is often constrained due to corresponding increases in toxicity overtime, most of the time damaging major organs or causing secondary malignancies. Accumulating evidence has shown that some natural products such as inositols and Genistein have signaling inducing effects both in-vivo and in-vitro in both cancer and in HIV. Their mechanism of actions appears to be made possible by site-specific action on multiple cellular signaling pathways without causing undesired toxicity in normal cells. Therefore, these non-toxic natural agents in a drink could be useful in combination with conventional chemotherapeutics and anti-virals, this can be used as preventive, or as an adjunct, or complementary.

Sun tanning is the result of sun radiation and free radical damage. This occurs when radiation from the sun is converted into oxygen-free radicals (reactive oxygen species, aka ROS) that damage the skin and its most of its support structure upon long term exposure. Free radical scavengers as well as myoinositol hexaphoshosphate (IP6) have been shown to neutralize this oxidative stress in the skin which can be caused by both UVA and UVB radiation and prevent three types of skin cancers.

According to the CDC, cigarette smoking is the number one risk factor for lung cancer. There are few targeted treatment options. In the United States, cigarette smoking causes about 90% of lung cancers. The world's two most populous nations—India and China—are home to more smokers than the entire population of the European Union. In China, more than 300 million people are tobacco users, while India adds another 275 million to the tally.

A study by the George institute of Global Health in 2010 revealed that the Asia-Pacific region is home to 30 percent of the world's smokers. The impact of smoking is greatest in these countries because smokers who develop lung cancer are diagnosed at later stages of the disease and receive less effective treatment. People who smoke are 15 to 30 times more likely to get lung cancer or die from lung cancer than people who do not smoke.

Existing literature has demonstrated a clear therapeutic benefit of inositol-1,2,3,4,5,6-hexakisphosphate, referred to herein as IP6, in high fiber diets and a growing number of scientific studies have demonstrated that IP6 has anti-proliferative and tumor suppressive properties and cancer prevention properties in numerous tumor types including skin cancers. The best human clinical evidence to date for cancer prevention in smokers using an oral pill form of administration is based on human clinical trials of smokers with dysplastic lung lesions that were reversed taking oral myoinositol.

Oral administration of IP6 has been shown to protect against lung and colon cancer and the prevention UVA/UVB induced skin tumors in basal, squamous, and melanoma skin tumors.

IP6 is a (poly) phosphorylated carbohydrate, ubiquitous in nature and synthesized in all animal cells. It functions as the principle storage form of phosphorous in many plants. It also occurs naturally in cereal grains, beans, brown rice, corn, sesame seeds, wheat bran, and other high fiber foods. Indeed, studies suggest that some of the health benefits afforded by eating a high fiber diet can be attributed to IP6 action. Copious amounts of high fiber is not practical for everyone and the human small intestine has very limited enzymes to break down this phosphate in order to reap the anti-cancer benefits associated with this compound. Furthermore, this phosphate gets bound to food proteins in the intestine and consequently largely gets degraded by stomach acids. Therefore a supplement for oral or an ionized aqueous administration having IP6 phytate is highly desirable.

Unlike rodents, the small intestine of humans express low levels of phytase, and this enzyme is required to metabolize IP6. Therefore, IP6 is not a source of dietary inositol and phosphate. Rather, myoinositol polyphosphates are synthesized within the body directly from phosphate and inositol, the latter being derived from glucose. IP6 ranges in concentration from 10 to 100 µM in mammalian cells. Importantly, phytic acid chelates several important minerals including zinc, iron, and to a lesser extent calcium and magnesium, although there is some debate regarding this issue for lack of evidence in vivo.

Inositol phosphates function as intracellular signaling intermediates that regulate a number of critical biochemical pathways in mammalian cells including cell cycle progression, cell differentiation, survival, migration, intracellular vesicle transport, metabolism and autophagy. Indeed, a key regulator of the activity of phosphatidylinositol (PtdIns) lipid substrates is the enzyme phosphatidylinositol 3-kinase (PI3K) which is the major cancer causing protein involved in all cancerous tumors. This enzyme phosphorylates the 3-OH residue of the myo-inositol ring of three specific PtdIns; phosphatidylinositol, phosphatidylinositol-4-phosphate, and phosphatidylinositol-4,5-bisphosphate. PI3K activity plays an important role in regulating the activity of other kinases that play important roles in metabolism and cell growth and survival including AKT (protein kinase B) and mTOR (mammalian target of rapamycin). Indeed, dysfunction and/or aberrant regulation of the PI3K pathway is implicated in cancers of the colon, breast, brain, liver, stomach, and lung. Therefore, development of potent and selective PI3K inhibitors as novel cancer therapeutics is currently the focus of intensive research efforts. However, first generation PI3K inhibitors developed in the art exhibited toxic side effects and poor pharmacological properties and selectivity, and as such were only effective in pre-clinical models. Alternatively, there exists a large amount of epidemiological data indicating that inositols are protective against certain forms of cancer. Indeed, a growing body of literature has linked the therapeutic benefits to natural products, such as IP6. Although IP6 has been shown to function as a free radical scavenger, other studies have demonstrated that it also functions as a PI3K inhibitor. Furthermore, several studies have shown that the ability of IP6 to block cell transformation or growth of tumor cells is directly related to inhibition of PI3K activity. For example, Huang et al. (1997) reported that IP6 at a concentration range of 0.5-2 mM showed a dose-dependent inhibition of EGF or TPA-induced cell transformation in JB6 cells as measured by three-dimensional growth in soft agar. This activity was linked to direct inhibition of PI3K. Similarly, Gu et al. (2009) showed that IP6-mediated growth inhibition of the prostatic adenocarinoma cell line PC-3 was correlated with reduced phosphorylation levels of the p85 subunit of PI3K at $Tyr^{458}$ and phosphoinositide-dependent kinase-1 PI3K1) at $Ser^{241}$. IP6 also caused a strong decrease in levels of integrin linked kinase 1 (ILK1) and cyclin D1 and reduced levels of phosphorylated AKT and GSK3α/β in these cells.

Based on these results and other data in both experimental animal models and human clinical trials demonstrating a therapeutic benefit of IP6 in preventing cancer, these products can be used as a prophylactic to protect against environmental insults that are implicated in tumor promotion via modulation of the PI3K/AKT/mTOR pathway.

More people die of lung cancer in the U.S. than any other type of cancer. This is true for both men and women. Most importantly, the overall 5-year survival rate for patients diagnosed with lung cancer is ~12% for men and ~16% for women. While smoking is the main cause of lung cancer, e.g. male and female smokers are 23 and 13 times more likely to develop lung cancer than non-smokers, respectively, 15% of all lung cancer patients have never smoked. Most importantly, no reliable metrics exists that can predict whether a smoker will develop lung cancer. Since most lung cancer patients are diagnosed with advanced disease, this knowledge is critical for developing adjuvant and front line therapies to improve survival of lung cancer patients.

Several studies have shown that myoinositol has protective effects in experimental models of lung cancer. For example, Estensen and Wattenberg reported that a diet containing 3% myo-inositol fed beginning 1 week after exposure to benzo[a]pyrene reduced the number of pulmonary adenomas by 40%.

These studies are significant in that benzo[a]pyrene is a polycyclic aromatic hydrocarbon found in automobile exhaust fumes, cigarette smoke, and charbroiled food metabolites, and its metabolites are both highly mutagenic and carcionogenic. Indeed, benzo[a]pyrene has been directly linked to lung and colon cancer. These results were confirmed by Hecht et al. and Witschi et al using a similar model of benzo[a]pyrene with or without 4-(methylnitrosamino)-1-(3-pyridyly)-1-butanone, the latter of which is also a component of cigarette smoke. Moreover, Witschi et al further demonstrated that a diet supplemented with 10 g per kilogram of myoinositol and 0.5 mg/kg dexamethasone (a steroid) produced a significant reduction in both lung tumor multiplicity and in tumor incidence as compared to a control diet in mice exposed to tobacco smoke. In these studies, mice were exposed to 71 mg total suspended particulates $(TSP)/m^3$ for the first two weeks, 86 $mg/m^3$ for three additional weeks, and 132 $mg/m^3$ for an additional 17 weeks for 6 hr per day, 5 days per week. In these studies, the diet containing myo-inositol/dexamethasone proved to be a highly effective chemopreventive regimen. The number of tumors per lung in animals fed myoinsoitol+dexamethasone and exposed to tobacco smoke actually approached the tumor multiplicity in animals exposed to filtered air.

Recently, a landmark study published by Gustafson et al. in the high impact journal *Science Translational Medicine* revealed that the PI3K pathway is activated in cytologically normal proximal airway epithelial cells in smokers with lung cancer and with dysplastic lesions. In these studies. PI3K activity was measured biochemically in airway biopsies by Western blot analysis and computationally by genome-wide micro-array analysis. This analysis revealed that the PI3K pathway was significantly up regulated in the airways of smokers with lung cancer as compared to controls, and genes that play a role in phosphatidylinositol signaling pathway were also significantly up regulated. Methodologies used to evaluate lung cancer patients were confirmed by demonstrating that PI3K signaling was also up regulated in basal-like and HER2-overexpressing breast tumors that lack PTEN function, a negative regulator of the PI3K pathway. Moreover, this analysis showed that the PI3K pathway signature was expressed at higher levels in lung tumors as compared to adjacent normal tissue, indicating that PI3K activation is important for lung cancer tumorigenesis.

The work by Gustafson at al. demonstrated that smokers with regression of dysplasia following treatment with myo-inositol showed significant (p<0.05) increased expression of genes that are repressed on PI3K activation in vitro, while smokers who did not respond to myo-inositol treatment had no change in the PI3K gene sets. The decrease in PI3K activity in patients who respond to myoinositol suggests that regression of dysplasia is associated with a reduction of PI3K pathway activity in the proximal airway. The authors subsequently showed that treatment of a lung adenocarcinoma cell line with myoinositol resulted in dose-dependent decreases in PI3K activity. Indeed, the median effective concentration (ECs) of myoinositol for PI3K inhibition was $7.3 \times 10^{-8}$ M. This $EC_{50}$ is comparable to the myoinositol doses given for regression of dysplastic lesions to high-risk smokers, which was 9 g twice daily (Lam S et al., 2006). These findings suggest that the cancer chemoprevention properties of myoinositol are most likely related to inhibition of PI3K activity.

Safety and efficacy of myoinositol has already been established in a Phase I clinical trial-Mayo Clinic (Lam et al. 2006). In this trial, sixteen smokers between 40 and 70 years of age with greater or equal to 30 pack-years of smoking history and one or more sites of bronchial dysplasia were enrolled in a dose escalation study of myo-inositol for one mouth. Subsequently, ten subjects were enrolled in a 3 month study employing the maximum tolerated dose, which was found to be 18 grams per day administered via oral administration. Side effects, when present, were mild and mainly gastrointestinal in nature. More importantly, a significant increase in the rate of regression of preexisting dysplastic lesions was observed (91% versus 48%; P=0.014) and a statistically significant reduction in the systolic and diastolic blood pressures by an average of 10 mm Hg was observed. Therefore, these data demonstrate that myoInositol in a daily dose of 18 grams per day for 3 months is safe and well tolerated and produces significant regression of pre-existing dysplastic lesions in smokers.

A wealth of epidemiological data exists showing that high-fiber diets are associated with lower risks of large intestinal cancer. Since IP6 levels are high in nuts and grains, several studies have directly evaluated the cancer fighting properties of IP6 in experimental animals of colon cancer. For example, Shamsuddin et al. (1988) first demonstrated that rats supplemented with 1% sodium IP6 before or two weeks post treatment with the carcinogen azoxymethane exhibited a 33% decrease in large intestinal cancer. A follow up study conducted by Shamsuddin and Ullah (1989) further showed that treatment of rats with IP6 was effective in significantly (p=0.02) reducing large intestinal cancers even when the treatment was begun 5 months after carcinogenic induction with azoxymethane. Consistent with these data, IP6 administration also reduced early biomarkers of colon cancer risk including the degree of aberrant crypt loci and labeling index of crypt cells in rodents (Jenab and Thompson, 1998; Norazalina et al., 2010). These studies are consistent with other reports indicating that IP6 inhibits growth of the human colon cancer cell lines in vitro (Sakamoto et al. 1993; Tain and Song, 2006), lowered their metabolic activity (Schroterova et al., 2010), and decreased the number of cells in S-phase by inducing G0/G1 arrest (El-Sherbiny et al. 2001).

TABLE A

Antitumor effect of inositol hexaphosphate (IP6) in-vitro

| Organ/Tissue | Species | Cell Line | Investigator |
|---|---|---|---|
| Blood | Human | Erythroleukemia K562 cell line, K562 1 human bone marrow | Shamsuddin et al Deliliers et al. ( |
| Colon | Human | Adenocarcinoma, HT-29 cell line | Sa Yang & Shamsuddin Samoto et al |
| Lung | Rat | Trachael epithelial + B[a]P | Arnold et al. |
| Liver | Human | Hep G2 cells | Vucenik et al. |
| Mammary | Human | Adenocarcinoma MCF-7, MDA-MB 231 cells | Shamsuddin et al. |
| Uterine cervix | Human | HeLa cells | Ferry et al. |
| Prostate | Human | Adenocarcinoma | Shamsuddin & |
|  | Human | P DU145 cells DC-3 cell line | Yang Zi et al. Singh et al. |
| Skin | Mouse | JB6 cells | Huang et al |
|  | Mouse | HEL-30 cells | Nickel & Belury Babich et al. |
|  | mice | melanoma line HTB68 also see references below for other skin cancer cell lines and investigator authors | Rizvi, et al |
| Soft tissue | Mouse | 3T3 fibroblast | Babich et al. |
|  | Human | Rhabdomyosarcoma, RD cells | Vucenik et al. |

Inositols are available as dietary supplements. IP6, inositol, and D-chiroinositol are sold in pill or powder form. Inositol and D-chiroinositol are advertised as members of the vitamin B complex (Vitamin $B_8$). However, this classification is outdated since they are produced from glucose in the body and as such are not essential nutrients. Inositol is advertised as useful in ameliorating symptoms associated with anxiety and depression. In double blinded clinical trials, D-chiro-inositol provided a substantial benefit to women with polycystic ovary syndrome (Nestler, 1999; Iuorno, 2002).

OBJECTS OF THE INVENTION

It is an object of the invention to provide a liquid and/or ionized aqueous product containing phosphated and/or pyrophosphated inositol isomers, particularly myoinositol hexaphosphate, and optionally containing Genistein and/or Ubiquinol as a dietary supplement and/or medical treatment.

It is another object of the invention to provide a liquid product containing Genistein, myoinositol hexaphosphate (and/or optical isomer thereof) together with myo-inositol (and/or optical isomer thereof) as a dietary supplement and/or as a medical treatment.

A still further object of the invention is to provide a liquid product as described in any of the foregoing objects of the invention which further contain a free radical scavenger.

Yet another object of the invention is to provide a liquid product as described in any of the foregoing objects of the invention further comprising at least one non-inositol B vitamin.

An even further object of the invention is to provide a liquid product as described in any of the foregoing objects of the invention further comprising at least one additional nutritional supplement or neutraceutical component.

A still further object of the invention is the use of any of the foregoing liquid products as a nutritional supplement in humans or animals.

Yet another object of the invention is the use of any of the foregoing liquid products in an oral method for the treatment, prevention, and/or reduction of risk of a cancer selected from the group consisting of skin (including squamous cell carcinoma, basal cell carcinoma, and melanoma), lung, pancreatic, breast, liver, blood, soft tissue, ovarian, prostate and/or colon cancers (see table and references) or in a method of the treatment of damage from or prevention of damage from or reduction of the risk of damage from reactive oxygen species in a human or animal in need thereof.

Still another object of the invention is the use of any of the foregoing liquid products in an oral neutraceutical or nutritional supplement product, where such product is used in a method for the treatment, prevention, and/or reduction of risk of a cancer selected from the group consisting of skin, lung, prostate, blood, wet tumors, and/or colon cancers, or in a method of the treatment of damage from or prevention of damage from or reduction of the risk of damage from reactive oxygen species in a human or animal in need thereof or as a nutritional supplement for use in the support of health with respect to any of the above.

Still other objects of the invention will be apparent to those of ordinary skill once having the benefit of the present disclosure.

DETAILED DESCRIPTION OF THE INVENTION

The present invention is an oral, aqueous liquid formulation containing one or more of a phosphorylated myoinsoitol (or optical isomer thereof), including without limitation the various mono-, di-, tri-, tetra-, penta-, or hexaphosphates or any mono-, di-, tri- or tetra-pyrophosphate groups, (or combinations thereof up to and including 9 phosphate groups, where a pyrophopsphate is counted as 2 phosphate groups). As used herein, when the term "inositol" is used without any designation as to the particular isomer involved it is to be construed as the genus of all 90f the optical isomers thereof unless the context of the particular sentence of paragraph require otherwise. The mono phosphates can be selected from those having the phosphate group at positions 1, 2, 3, 4, 5, or 6 of the inositol 6 member ring. The di-monphosphates can be selected from the those having the 1,2-, 1,3-, 1,4-, 1,5-, 1,6-, 2,3-, 24-, 2,5-, 2,6-, 3,4-, 3,5-, 3,6-, 4,5-, 4,6-, and 5,6-diphosphate substitution pattern. The tri-monophosphates can be selected from those having the 1,2,3-, the 1,2,4-, 1,2,5-, 1,2,6-, 2,3,4-, 2,3,5-, 2,3,6-, 2,4,5-, 2,4,6-, 2,5,6-, 3,4,5-, 3,4,6-, and 4,5,6-trimonophosphate substitution pattern. The tetramonophosphates can be selected from those having the 1,2,3,4- 1,2,3,5-, 1,2,3,6-, 1,2,4,5-, 1,2,4,6-, 1,3,4,5-, 1,3,4,6-, 1,4,5,6-, 2,3,4,5-, 2,3,4,6-, 2,4,5,6-, and 3,4,5,6-tetramonophosphate substitution pattern. The pentamonophosphates can be selected from those having the 1,2,3,4,5-, 1,2,3,4,6-, 1,2,3, 5,6-, 1,2,4,5,6-, 1,3,4,5,6-, and 2,3,4,5,6-pentamonophosphate substitution pattern. The pyrophosphated inositols can be selected from those having up 1-4 pyrophosphate groups. The monopyrophosphates can be selected from those having the pyrophosphate group at positions 1, 2, 3, 4, 5, or 6 of the inositol 6 member ring. The di-pyrophosphates can be selected from the those having the 1,2-, 1,3-, 1,4-, 1,5-, 1,6-, 2,3-, 24-, 2,5-, 2,6-, 3,4-, 3,5-, 3,6-, 4,5-, 4,6-, and 5,6-dipyrophosphate substitution pattern. The tri-pyrophosphales can be selected from those having the 1,2,3-, the 1,2,4-, 1,2,5-, 1,2,6-, 2,3,4-, 2,3,5-, 2,3,6-, 2,4,5-, 2,4,6-, 2,5,6-, 3,4,5-, 3,4,6-, and 4,5,6-tripyrophosphate substitution pattern. The tetrapyrophosphates can be selected from those having the 1,2,3,4- 1,2,3,5-, 1,2,3,6-, 1,2,4,5-, 1,2,4,6-, 1,3, 4,5-, 1,3,4,6-, 1,4,5,6-, 2,3,4,5-, 2,3,4,6-, 2,4,5,6-, and 3,4, 5,6-tetrapyrophsophate substitution pattern. Combinations of monophosphate and pyrophosphate substitutions in a single compound are also possible and may be selected from any of the mono-monophosphates, di-monophosphates, tri-monophosphates, tetramonophosphates, and pentamonophosphates mentioned above having pyrophosphate groups on any of the remaining available positions that are not monophosphated so long as the number of monophosphate groups+twice the number of pyrophosphate groups does not exceed 9. Preferably, the phosphorylated compounds are selected from tetra-monophosphate, penta-monophosphate, hexamonophosphate, petamonophosho-monopyrophosphate, and tetrmonophophospho-dipyrophosphate. Particularly preferred are myoinositol hexaphosphate (IPO), myoinositol pentaphosphate, myoinositolpentamonophospho-monopyrophosphate, myoinositoltetramonophospho-dipyrophosphate, the corresponding phosphated (inclusive of pyrophosphorylated) D-chiroinositol analogs thereof, and the corresponding phosphated (inclusive of pyrophosphorylated) scylloinositol analogs thereof. The phosphorylated inositol component is in an effective amount as a nutritional supplement; and/or an effective amount as a medicinal for the treatment of, prevention of, or reduction of the risk of developing a cancer including, without limitation, of the skin, lung, multiple myeloma, leukemia, prostate, ovarian, pancreatic, breast, liver, throat, even viral HPV induced throat cancer, or colon; and/or an effective amount for the treatment of, prevention of, and/or reduction in the risk of damage to cells caused by reactive oxygen species (ROS). Other utilities and aspects of the present invention include protection of those going to high elevations (particularly pilots, extreme mountain climbers, as well as astronauts) as a protectant prophylactically against radiation exposure due to lesser protective effects of the atmosphere against ambient radiation, and environmental toxins. i.e., car exhaust, pollution, radiation, and known toxic free radical generating chemicals. (One particularly troublesome group of compound in the environment includes phthalates, which are known to generate free radical oxygen species in-vivo, and thus, the present invention is useful to offset the undesirable effects thereof.) Similarly, the present invention is also useful as a prophylactic measure against some of the accidental or routine radiation exposure involved with nuclear power plant operators and those involved in mining and refining of radioactive materials. It should be realized that the present invention is not expected to fully cure or fully prevent such effects of radiation exposure, but is of use in minimizing or reducing the effects that would result in the absence of use of the invention or any other preventative measure. Still further utilities for the present invention include usage before, during, or after radiation treatments, which radiation treatments are either for disease treatment (as in radiation for cancer therapy) or diagnostic purposes, such as CAT scans, X-rays, etc., as a partial protectant against at least some of the undesirable effects of such radiation exposure. Human exposure to urban air pollution may trigger toxic responses in brain cells, impacting neurodegenerative disease pathways. As such, the present invention is of use in the prevention and/or treatment of neurodegenerative disease states such as, without limitation, Alzheimer's and brain tumors. A particularly preferred non-limiting embodiment for such neurodegenerative conditions is one which utilizes at least one inositol or inositol phosphate(s) having the scylloinositol optical isomer configuration.

In addition to the phosphorylated inositol (any inoitol isomer) component and water, the formulations optionally may also contain, one or more of (any) unphosphorylated inositol. (in one non-limiting embodiment, the unphosphorylated inositol is myoinositol and the phosphorylated inositol is myoinositol hexaphosphate.) Still further optional components of the present formulation include nutritionally acceptable monovalent electrolytes (including without being limited thereto, cations such as, without limitation sodium, and potassium, and anions such as, without limitation chloride; non-limiting examples of which include sodium chloride, and potassium chloride) as are known in the nutritional supplement arts and/or vitamins (including, without limitation thereto the B vitamins (including without limitation thiamine (vitamin B1); riboflavin (vitamin B2); niacin and/or nicotinamide (vitamin B3); pantothenic acid (vitamin B5); pyridoxine, pyridoxal, pyridoxamine, and/or pyridoxine HCl (vitamin B6); biotin (vitamin B7); folic acid (vitamin 89), and cobalamine (vitamin 812) and vitamin C), as well as herbal extracts. (Nutritionally available salts and esters of the various vitamins may be used in place of the specifically stated vitamin.) The above vitamins and electrolytes are used in amounts such that from 1 to 4 doses (whether as 30 ml, 60 ml, 90 ml, 120 ml, 150 ml, 180 ml, or 240 mil per dose) delivers from %/4 to the full US RDA independently for each one present in a particular formulation (although lesser amounts are acceptable but just not preferred). The formulations of the invention may also optionally contain one or more of flavors (such as without limitation, coconut, grape, blueberry, pomegranate, apple, strawberry, kiwi, dragonftuit, lemon, lime, raspberry, mango, etc), sweeteners (such as without limitation, sucrose, fructose, glucose, stevia, aspartame, rebaudioside A, sucralose, mannitol, xylitol, syrups, etc.), colorings, stabilizers, pH adjusters, preservatives (such as without limitation, sodium benzoate), etc, as well as thickeners and processing aids as may be generally known in the beverage and/or liquid nutritional supplement arts in amounts generally known as acceptable in the art.

Effective amounts of the phosphorylated inositol component (or optical isomers thereof, when used without other inositol components range from about 0.5 to about 4% (w/v), preferably about 0.75 to about 3% w/v, more preferably about 1 to about 2.5% w/v, still more preferably about 1.1 to about 2% w/v, even more preferably 1.2 to about 1.5% w/v, and most preferably about 1.25% w/v, most preferable & effective dose 2%-4% (w/v) phosphorylated inositol with a daily dosing typically in the range such that about 0.5 to about 18 grams per day, preferably about 1.0 to about 15 grams per day, more preferably about 1.2 to about 10 grams per day, still more preferably about 2.4 to about 8 grams per day, yet more preferably about 3.6 to about 7 grams per day, and most preferably about 4.8 grams to about 5.5 grams per day of phosphorylated inositol is administered. When combined with myoinositol, the phosphorylated component is combined with the unphosphorylated inositols (preferably myoinositol) in a ratio of the phosphorylated component to unphosphorylated inositols (most preferably myoinositol) of about 6:1 to 1:6, preferably about 5:1 to about 1:5, more preferably about 4:1 to about 1:4, still more preferably about 3:1 to about 1:3, even more preferably about 2:1 to about 1:2, most preferably about 1:1, each being a molar ratio. Other suitable ratios include, without limitation, preferably about 4.5:1 to about 1:1, more preferably about 4.25:1 to about 3:1, still more preferably about 4:1 of the phosphorylated inositol component to unphosphorylated inositols (a non-limiting preferred being myoinositol) on a molar basis. Nonetheless, the specific concentration in a given drink may be more or less (including multiple times or fractions thereof (if the volume of the drink per daily dose is properly adjusted to compensate therefore). Thus, for example, for a 1.25% w/v solution of myoinositolhexaphosphate (IP6), where a drink is intended to deliver 3000 mg/240 ml with a serving or dose size of 240 ml (i.e. to deliver a 6 g dose of myoinositol hexaphosphate in two 240 ml doses, typically administered as 240 ml twice daily), an alternate drink having 1500 mg/120 ml with a serving or dose size of 120 ml (either taken 4 times a day or in the situation where a lower dosing is desired, less frequently), or another alternate of 62.5 mg/5 ml where significantly lower amounts are desired. Adjustment of dosings for smaller than average or larger than average adults or for adolescents or children will generally be within the skill of one of ordinary skill in the art given the foregoing ranges for a typical adult. When used in combination with other inositol species, the specific amount of phosphorylated component may be reduced somewhat, but preferably, the other inositol species are added to the above mentioned amounts of the phosphorylated component. In one particularly preferred embodiment, the invention has myoinositolohexaphosphate optionally with or without myoinositol as the only inositol species. When an IP6 is used in combination with an unphosphorylated inositol, the most preferred ratio is stated above is a molar ratio of 1:1 and in a most preferable, but non-limiting embodiment, the total daily dose of such a ratio is about 4.8 grams of the myoIP6 (or isomer thereof) together with 1.32 grams of the unphosphorylated myoinositol (or isomer thereof).

As to the inositol optical isomers that may be used for the invention there are myoinositol, scylloinositol, mucoinositol. D-chiroinositol, L-chiroinositol, neoinositol, alloinositol, epiinositol, and/or cisinositol, with myoinositol, and D-chiroinositol being preferred and myoinositol being most preferred. As to the isomers of the phosphorylated inositol component, one may use the any of the phosphates and pyrophosphates set forth in paragraph 0031 above with any of the inositol optical isomers of the preceding sentence, with myoinositol hexaphosphate, D-chiroinositol hexaphosphate, and scylloinositol hexaphopshate being non-limiting preferred species and myoinositol hexaphosphate being a non-limiting most preferred species.

As the optional free radical scavengers, any orally acceptable free radical scavenger known in the art is a is acceptable for use in the present invention, for example, without limitation, N-Acetyl-L-cysteine. L-Ascorbic acid. Balsalazide (typically available as the disodium salt hydrate), Caffeic acid, (−)-Catechin gallate, Chlorogenic acid, Delphinidin chloride, Diosmin, Ellagic acid, (−)-Epicatechin, Fucoxanthin carotenoid antioxidant. (−)-Gallocatechin, (−)-Gallocatechin gallate, Gallic acid, Ginkgolide B, 3-Hydroxytyrosol, Luteolin, Lycopene, Neochlorogenic acid, Resveratrol, Rutin hydrate, Seleno-L-methionine, Se-(Methyl)selenocysteine hydrochloride, Ubiquinol (liposomal encapsulated Qunol) CoQ10, and Sodium selenite, most preferably L-ascorbic acid. The optional orally acceptable free radical scavengers can be used in amounts generally known as acceptable in the art; when ascorbic acid is used, it is preferably present in amounts of about 30 mg/120 ml of solution (i.e., about 0.025% w/v) or 60 mg/120 ml of solution (about 0.05% w/v). Although, optional, of these, Ubiquinol in an orally administrable, absorbable form is a non-limiting, but particularly preferred species. Such orally administrable and absorbable forms of Ubiquinol are set forth in U.S. Pat. No. 6,455,072 which is incorporated herein in its entirety by reference. When used, the Ubiquinol is present in an amount of up to about 300 mg Ubiquinol per dose, preferably up to about 250 mg, more preferably up to 200 mg. In other embodiments, the Ubiquinol is present in at least 50 mg/dose, at least 100 mg/dose, and most preferably at about 200 mg/dose.

An additional known free radical/reactive oxygen scavenger, for use in the present invention is Genistein. In the present invention, when Genistein is used, it is used in amounts in the range (in mg/kg/day) of from a lower end of about 1 to about 5 mg to an upper range end of about 10 to about 50 mg. Exemplary dosing ranges (in mg/kg/day) include (without limitation) those with a range lower limit of about 1 mg, about 2 mg, about 3 mg, about 4 mg, about 5 mg, about 6 mg, about 7 mg, about 8 mg, about 9 mg, about 10 mg, about 12.5 mg, about 15 mg, about 17.5 mg, about 20 mg, about 25 mg, about 30 mg, about 35 mg, and about 40 mg and having an upper end point of the range selected from about 10 mg, about 12.5 mg, about 15 mg, about 17.5 mg, about 20 mg, about 25 mg, about 30 mg, about 35 mg, about 40 mg, about 45 mg, and about 50 mg. Within these ranges, preferred dosages are in the range (in mg/kg/day) of about 1 to about 30 mg, more preferably about 2 to about 20 mg, still more preferably about 3 to about 15 mg, even more preferably about 5 to about 12.5 mg, most preferably about 10 mg. In the present invention, when Genistein is used, it is used in combination with one or more the other inositiol isomers and/or the inositol hexaphosphate isomers mentioned herein, preferably the Genistein is used in combination with at least one unphosphorylated inositol isomer and at least one phosphorylated inositol isomer, most preferably at least one of a tetramonophosphate, a pentamonophosphate, a hexamonophosphate, a pentamonophospho-monopyrophosphate, a tetramonophospho-dipyrophosphate of at least one inositol isomer. In some particulaily preferred embodiments myoinsitol hexaphosphate and myoinositol is used. In others, the corresponding hexaphosphate and unphosphorylated combination of the other inositol isomers are used in which the phosphphorylated component is the hexaphosphate of the unphosphorylated inositol used. Whether the Genistein is used in combination with inositols which are (a) only phosphorylated inositol isomers, or (b) combinations of unphosphorytlated inositol isomers AND phosphorylated inositol isomers, the benefits of the invention may be obtained. The non-limiting preferred unphosphorpylated inositol isomers for the Genastein containing embodiments are selected from myoinositol, D-chiroinositol, and scylloinositol. Independently, the preferred phosphorylated inositol isomers for use in the Genistein containing embodiments are selected from myoinositol phosphates, D-chiroinositol phosphates, and scylloinositol phosphates (each inclusive of the full range of monophosphato and pyrophosphate- and mixed monophosphato-pyrophosphato groups set forth above). These Genistein and Insoitol isomeric combinations (whether phosphorylated or unphosphorylated or both) may be used as is or in combination with the other (non-inositol type) components (mentioned herein) in analogous manners as set forth herein with respect to the compositions that do not mention Genistein specifically.

The combination use of Genistein and the inositols and/or the inositol phosphates as described above gives rise to the ability to prevent, delay, modulate, reduce, and treat HIV infections, in a substantially enhanced, substantially non-toxic manner, especially as compared to current medicinal agents for use in the treatment and prophylaxis for HIV. Neither the inositol components nor the Genistein component have the known side effects or associated drug toxicities' and/or drug resistance known to occur with current drugs used to treat HIV and/or AIDS cancers and disseminated diseases due to being plant-based, will likely side step the toxicity issues faced with current drugs, a common occurrence or by product of the everyday and life-long use of the pharmaceutical based regimen faced by HIV positive individuals. This product can be preventive, also an adjunct and/or complementary treatment because patients over time do become resistant to their drugs due to HIV mutant infections known to occur in this disease as well as in cancer. Without being confined to the theory, it is believed that instead of acting directly with the virus, Genistein blocks the many cellular processes that appear to be necessary for the virus to infect cells by inducing a conformational change. This conformational change and signal block works along with the inositol isomer components (whether or not phosphorylated) in a synergistic manner with lesser side effects, and better compliance and better user acceptability to achieve positive outcomes in both cancer and HIV. This allows for impeding viral DNA synthesis and cancer growth and/or impeding viral nuclear migration so that the invention Genistein containing compositions can be used in the prevention, treatment, and amelioration of HIV infection of immune cells, especially resting CD4 T-cells.

The present invention offers phosphorylated inositols in an aqueous oral form as a means to reap the therapeutic benefits of this natural product, particularly in lieu of or in addition to a diet high in fiber. One of the advantages of the present invention is that the delivery of undigested phytate IP6 and the other inositol species are in a form in which they are not captured and broken down as readily as solid forms containing these agents.

As previously described, the present invention formulation is used for an oral delivery of the active agents therein for the prevention and/or treatment and/or reduction of the risk of developing cancers such as, without limitation, one or more of skin cancer (inclusive of squamous, basal, and melanoma), breast, prostate, ovarian, pancreatic, lung cancer, colon cancer liver cancer, bone cancer, soft tissue cancer, muscular cancer (such as without limitation,) or a blood cancer (such as without limitation a leukemia)(or as described in Table A above) and/or treatment of damage and/or prevention of damage and/or reduction of the risk of damage to cells by reactive oxygen species free radicals that are generated in the body due to environment or metabolic insult. Environmental or metabolic insult may arise from exposure to a wide variety of factors, including radiation, known carcinogens, and known free oxygen radical generating substances (such as in, without limitation, cigarette smoke, pollutants, radiation exposure (whether natural, or created in the workplace, or incident to diagnostic tests and medical treatments, etc.). For the above purposes, a suitable (non-limiting, exemplary) dose of a formulation of the present invention having about 1% to about 4% w/v of myoinositol hexaphosphate (and/or optical isomer thereof) or other phosphorylated species of myoinositol or its isomers as set forth above (mono-nona phosphates) therein in an amount of about 30 ml to about 480 ml, preferably about 60 ml to about 360 ml, more preferably 90 ml to about 270 ml, still more preferably 360 ml, about 120 ml to about 240 ml, most preferably about 180 ml to about 240 ml at least once to 2 times per day, with variations thereon that will be recognized by those of ordinary skill in the art for delivery of about 3 g to about 9 g of myoinositol hexaphosphate (and/or optical isomers thereof) or of the other corresponding phosphates having from 1 to 9 phosphate groups (inclusive of those having pyrophosphate groups in which each pyrophosphate is counted as two of the up to 9 phosphates) on a daily basis for an average adult in 1-2 or 2-4 divided doses a day.

The formulations of the present invention most preferably have the inositol components thereof in solution and preferably are clear, although non-inositol portions of the formulation may make the solution less than completely clear without departing from the invention.

The following non-limiting examples are exemplary only and do not have any limiting effect on the present invention.

Example 1

The following Table I represents a set of inositol hexaphosphate isomers (alone or with an unphosphorylated inositol) for use in the present invention. Table II specifies amounts of the hexaphosphated inositol and the unphosphorylated inositol components, and each is applied independently to the 90 combinations in Table I. For clarity, all of the "A" cells in Table 1 have the respective hexaphosphate mentioned in the left hand column with no unphosphorylated inositol component. All of the "B" cells of Table I have the respective hexaphosphate in combination with unphosphorylated myo-inositol.

TABLE I

| Hexaphosphate Component | Unphosphphorylated Component | | | | | | | | | |
|---|---|---|---|---|---|---|---|---|---|---|
| | A | B | C | D | E | F | G | H | I | J |
| 1. Myo-inositol Hexaphosphate | None | Myo-inositol | Scyllo-inositol | Muco-inositol | D-chiro-inositol | L-chiro-inositol | Neo-inositol | Allo-inositol | Epi-inositol | Cis-inositol |
| 2. scyllo-inositol Hexaphosphate | None | Myo-inositol | Scyllo-inositol | Muco-inositol | D-chiro-inositol | L-chiro-inositol | Neo-inositol | Allo-inositol | Epi-inositol | Cis-inositol |
| 3. Muco-inositol Hexaphosphate | None | Myo-inositol | Scyllo-inositol | Muco-inositol | D-chiro-inositol | L-chiro-inositol | Neo-inositol | Allo-inositol | Epi-inositol | Cis-inositol |
| 4. D-chiro-inositol Hexaphosphate | None | Myo-inositol | Scyllo-inositol | Muco-inositol | D-chiro-inositol | L-chiro-inositol | Neo-inositol | Allo-inositol | Epi-inositol | Cis-inositol |
| 5. L-chiro-inositol Hexaphosphate | None | Myo-inositol | Scyllo-inositol | Muco-inositol | D-chiro-inositol | L-chiro-inositol | Neo-inositol | Allo-inositol | Epi-inositol | Cis-inositol |
| 6. Neo-inositol Hexaphosphate | None | Myo-inositol | Scyllo-inositol | Muco-inositol | D-chiro-inositol | L-chiro-inositol | Neo-inositol | Allo-inositol | Epi-inositol | Cis-inositol |
| 7. allo-inositol Hexaphosphate | None | Myo-inositol | Scyllo-inositol | Muco-inositol | D-chiro-inositol | L-chiro-inositol | Neo-inositol | Allo-inositol | Epi-inositol | Cis-inositol |
| 8. epi-inositol Hexaphosphate | None | Myo-inositol | Scyllo-inositol | Muco-inositol | D-chiro-inositol | L-chiro-inositol | Neo-inositol | Allo-inositol | Epi-inositol | Cis-inositol |
| 9. Cis-inositol Hexaphosphate | None | Myo-inositol | Scyllo-inositol | Muco-inositol | D-chiro-inositol | L-chiro-inositol | Neo-inositol | Allo-inositol | Epi-inositol | Cis-inositol |

TABLE II

| % are w/v unless noted otherwise | | | | | | | | | |
|---|---|---|---|---|---|---|---|---|---|
| | I | II | III | IV | V | VI | VII | VIII | IX |
| Hexaphosphated inositol of Table I | 1% | 2% | 4% | 1% | 2% | 4% | 1% | 2% | 4% |
| Unphosphorylated inositol of Table I When present* | 0.135% | 0.27% | 0.54% | 0.27% | 0.54% | 1.08% | 0.54% | 1.08% | 2.16% |
| Ascorbic acid | 0.025% | 0.025% | 0.025% | 0.05% | 0.05% | 0.05% | 0.1% | 0.1% | 0.1% |
| Water | qs to 240 ml. | qs to 240 ml. | qs to 240 ml. | qs to 240 ml. | qs to 240 ml. | qs to 240 ml. | qs to 240 ml. | qs to 240 ml. | qs to 240 ml. |

*Molar ratios of hexaphosphates to unphosphorylated inositol in above Table II are either 0.5:1 or 1:1, or 2:1

Each of the 810 formulations resulting from Tables I and II are packaged for introduction into the marketplace. For the sake of clarity, a Table I cell 1B Table II Col I formulation has 1% myoinositol hexaphosphate; 0.135% myoinositol.

Example 2

The following Table 11 utilizes each of the separate formulations of Example 1 except that additional nutritional supplement components are added. The amounts in Table III are expressed as % of the US Recommended Daily Allowance (USRDA) for the particular component in question, or if in mg, then mg/240 ml of solution.

TABLE IIIA

| Vitamin Or electrolyte | a | b | c | d | e | f | g | h | i |
|---|---|---|---|---|---|---|---|---|---|
| B1 | 5% | 10% | 15% | 20% | 5% | 10% | 15% | 20% | 5% |
| B2 | 5% | 10% | 15% | 20% | 5% | 10% | 15% | 20% | 5% |
| B3 | 5% | 10% | 15% | 20% | 5% | 10% | 15% | 20% | 5% |
| B5 | 5% | 10% | 15% | 20% | 5% | 10% | 15% | 20% | 5% |
| B6 | 5% | 10% | 15% | 20% | 5% | 10% | 15% | 20% | 5% |
| B7 | 5% | 10% | 15% | 20% | 5% | 10% | 15% | 20% | 5% |
| B9 | 5% | 10% | 15% | 20% | 5% | 10% | 15% | 20% | 5% |
| B12 | 5% | 10% | 15% | 20% | 5% | 10% | 15% | 20% | 5% |
| sodium | 110 mg | 110 mg | 110 mg | 110 mg | 110 mg | 110 mg | 110 mg | 110 mg | 110 mg |
| potassium | 450 mg | 450 mg | 450 mg | 450 mg | 450 mg | 450 mg | 450 mg | 450 mg | 450 mg |

Each of the formulations in Tables I-IIIA have the further optional electrolytes and supplemental components such as preservatives and stabilizers added in accordance with Table IIIB. Each of the resulting solution is bottled for distribution.

TABLE IIIB

| Component | i | ii | iii | iv | v | vi | vii | viii | ix |
|---|---|---|---|---|---|---|---|---|---|
| sodium | none | 55 mg | 110 mg | 220 | none | 55 mg | 110 mg | 220 | 110 mg |
| potassium | none | none | none | none | 450 mg | 450 mg | 450 mg | 450 mg | 450 mg |
| Sodium benzoate | None | 0.1% | 0.1% | 0.1% | 0.1% | 0.1% | 0.1% | 0.1% | 0.1% |
| malic acid | none | 250 mg | 250 mg | 250 mg | 500 mg | 500 mg | 500 mg | 500 mg | 1000 mg |

Example 3

A single specific formulation of the invention comprises:
distilled water
1:1 molar ratio Myo-Inositol hexaphosphate (myo-IP6), (4.8 grams) and myo-inositol (1.32 grams),
crystalline fructose,
citric acid (preservative),
vegetable juice (color),
natural flavor,
ascorbic acid (vitamin C),
sodium citrate (electrolyte/antioxidant),
monopotassium phosphate
niacin (13),
pantothenic acid (B5),
pyridoxine hydrochloride (B6),
cyanocobalamine (B12)
The above components are dissolved in the water and bottled for distribution.

Example 4

A particular formulation of the invention comprises
Carbonated water-Carbon dioxide,
Inositol hexaphosphate (4.8 grams) and myo inositol 1.32 grams (1:1 molar ratio),
Erythritol (Rebiana™),
citric acid (preservative),
vegetable juice (color),
natural flavor.
artificial flavors.
ascorbic acid (vitamin C),
sodium citrate (electrolyte),
Monopotassium Phosphate
niacin (B3),
pantothenic acid (B5),
pyridoxine hydrochloride (B6),
cyanocobalamine (B12)
The above components are dissolved in the water and bottled for distribution.

Example 5

A particular formulation of the invention comprises
Distilled and/or sterilized community tap water.
Myo inositol (4.8 grams)
granulated table sugar (14 grams),
citric acid,
high fructose corn syrup,
colors.
glucose,
fructose.
sodium citrate (preservative).
vegetable juice (color).
natural flavor,
ascorbic acid (vitamin C),
natural flavor,
sodium citrate (electrolyte),
monopotassium phosphate (electrolyte),
niacin (B3),
pantothenic acid (B5),
pyridoxine hydrochloride (B6),
cyanocobalamine (B12)
sufficient sodium chloride to bring the sodium content up to 110 mg/240 ml, The above components are dissolved in the water and bottled for distribution.

Example 6

800 mg of myoinositol hexaphosphate and 220 mg of myoinositol were dissolved in 240 ml of distilled water to form a drink product of the present invention. The drink product was consumed twice a day.

Example 7: Bottled Water of the Invention

Water, if not already either purified, distilled, or filtered is subjected to an operation to obtain the water in a purified, distilled, or filtered state, and if need be stored for future use. The water is then used to dissolve the components of one of the foregoing formulations, and the result is bottled into appropriate containers.

Example 8: Bottled Carbonated Soft Drink of the Invention

Purified, distilled, or filtered water as obtained in the initial step of Example 7 is used placed in a mixing tank. The various components of the son drink, which typically do not include the inositol components of the present invention, typically sweeteners, "soft drink concentrate", and flavor are added to the mixing tank. The inositol and hexaphosphate inositol components, either as dry powders or concentrate solutions in water are added to the mixing tank in one embodiment before "soft drink components" or thereafter in a second embodiment. The solution is then subjected to a carbonation process and the result is bottled in suitable containers.

Example 9: Bottled Ready to Drink Tea of the Invention

A typical available ready to drink tea of the invention is prepared by preparing such tea in the ordinary fashion for such tea and subjecting the tea to a pasteurization process. The components of the present invention other than the tea are added thereto (as powders) under aseptic bottling conditions or alternatively the components of the present invention other than the tea are dissolved in purified, distilled, or filtered water at high concentrations, subjected to aseptic filtration, and the aseptically filtered solution is added to the pasteurized tea under aseptic conditions.

Example 10: Bottled Juice Drink of the Invention

A bottled fruit juice of the invention can be prepared by merely taking an existing fruit juice drink after it has been pasteurized and fortifying it under asceptic conditions with the inositol hexaphosphate or a mixture of inositol hexaphosphate and inositol and continue to bottle it in appropriate containers under aseptic conditions.

Example 11

Inositol hexaphosphate and inositol enriched soft and hard drinks

Myo-inositol hexaphosphate and myo-inositol in a 1:1 molar ratio are added to known bottled soft (including bottled water) and/or hard drinks, including those marketed under various trade names including those products made or distributed under various Coco-Cola™ brands, Aquapure, Aquarius, Bacardi Mixers. Bacardi Premium Mixers, Barq's, Barrilitos, Beverly, Bright And Early, caffeine free Barq's, caffeine free Coca-cola, caffeine free Coke light/Diet Coke, Campbells, Cascal, cherry Coke, Chippewa, Citra, Coca-cola, Coca-Cola Zero, Cumberland Gap, DANNON*, DASANI, Delaware Punch, diet_Barq's, Diet cherry Coke, Diet Coke/Coca-Cola light, Diet Coke/Coca-Cola light with Lime, diet Fanta, diet Inca Kola, diet Mello Yello/Mello Yello Zero, Diet NESTEA*, diet Vanilla Coke, Dr Pepper. Evian, Fanta, Five Alive, Flavor Rage, Fresca, Fruitopia, FUZE, Georgia, glacéau smart water, glacéau vitamin water, glacéau vitamin water zero, Gold Peak. H2OK, Hi-C, Honest, Illy*, Inca Kola, Java Monster, Juan Valder, Krest, Lift, Master Chill, Master Pour, McCafe, Mello Yello, Mero Mix. Minute Maid, Minute Maid Enhanced, Minute Maid Juices To Go, Minute Maid Soft Drink, Monster, NESTEA*, NESTEA COOL*, Northern, Neck, NOS, Odwalla, Peace, Pepe Rico, Pibb, POWERADE, POWERADE LIGHT, POWERADE PLAY, Red Flash, Simply Orange, Smart, Sokenbicha, Southern Sun, Sprite, Sprite Remix, Sprite Zero/diet Sprite/Sprite light, Sunfill, TaB, Vanilla Coke, VAULT, Vegitabeta, Worx, Energy. Zico, all Pepsi brands and Gatorade brands.

Inositol phosphates and/or analogs described herein are excellent candidates for chemoprevention due to cell permeability, solubility, low toxicity, and demonstrated efficacies inhibiting tumor growth.

Example 12: Genistein Containing Compositions

Examples 1-5 and 7-11 are repeated except that 1 mg (Example 12a), 5 mg (Example 12b), 10 mg (Example 12c), 15 mg (Example 12d), 20 mg (Example 12e), 25 mg (example 12f), 30 mg (Example 12g), 35 mg (Example 12h), 40 mg (Example 12i), 45 mg (Example 12j) or 50 mg (Example 12k) of Genistein are added to the compositions. Each subpart of Example 12 is to be understood as a repetition of each of Examples 1-11 with the particular amount of Genistein mentioned for that subpart.

Example 13

500 mg of myoinositol hexaphosphate and 1.67 grams myoinositol, 20 mg's of Genistein were dissolved in 20 oz of distilled water to form a drink product of the present invention. The drink product was consumed twice a day.

Example 14

500 mg of myoinositol hexaphosphate and 1.67 grams myoinositol, 20 mg's of Genistein, 200 mgs of pharmaceutical grade water soluble liposomal encapsulated Ubiquinol (Qunol Liquid Co Q10) (U.S. Pat. No. 6,455,072) were dissolved in 20 oz of distilled water to form a drink product of the present invention. The drink product was consumed twice a day.

Example 15

500 mg of myoinositol hexaphosphate and 1.67 grams myoinositol, 20 mg's of Genistein, pharmaceutical grade water soluble liposomal encapsulated-Ubiquinol (Qunol Liquid Co Q10) (U.S. Pat. No. 6,455,072) were dissolved in 20 oz of Acai blueberry Pomegranate juice to form a drink product of the present invention. B1 1.1 mg. B5 5 mg B6-1.7 mg. B12-2.4 mcg, ascorbic acid-500 mg tablets were crushed and added to the drink- and the drink product was consumed twice a day.

Example 16

Examples 1-5 and 7-12 are repeated except that the hexaphosphate of the respective inositol is replaced by the phosphate in the following table.

| Example | Type of phosphate material | Species of phosphate |
|---|---|---|
| Example 16A | monophosphate | 1-monophosphate; 2-monophosphate; 3-monophosphate; 4-monophosphate; 5-monophosphate; 6-monophosphate |
| Example 16B | di-monophosphate | 1,2-dimonophosphate; 1,3-dimonophosphate; 1,4-dimonophosphate; 1,5-dimonophosphate; 1,6-dimonophosphate; 2,3-dimonophosphate; 2,4-dimonophosphate; 2,5-dimonophosphate; 2,6-dimonophosphate; 3.4-dimonophosphate; 3,5-dimonophosphate; 3,6-dimonophosphate; 4,5-dimonophosphate; 4,6-dimonophosphate; 5,6-dimonophosphate |
| Example 16C | Tri-monophosphate | 1,2,3-trimonophosphate; 1,2,4-trimonophosphate; 1,2,5-trimonophosphate; 1,2,6-trimonophosphate; 2,3,4-trimonophosphate; 2,3,5-trimonophosphate; 2,3,6-trimonophosphate; 2,4,5-trimonophosphate; 2,4,6-trimonophosphate; 2,5,6-trimonophosphate; 3,4,5-trimonophosphate; 3,4,6-trimonophosphate; 4,5,6-trimonophosphate |
| Example 16D | Tetra-monophosphate | 1,2,3,4-tetramonophosphate; 1,2,3,5-tetramonophosphate; 1,2,3,6-tetramonophosphate; 1,2,4,5-tetramonophosphate; 1,2,4,6-tetramonophosphate; 1,3,4,5-tetramonophosphate; 1,3,4,6-tetramonophosphate; 1,3,5,6-tetramonophosphate; 2,3,4,5-tetramonophosphate; 2,3,4,6-tetramonophosphate; 2,4,5,6-tetramonophosphate; 3,4,5,6-tetramonophosphate |
| Example 16E | Penta-monophosphate | 1,2,3,4,5-pentamonophosphate 1,2,3,4,6-pentamonophosphate 1,2,3,5,6-pentamonophosphate 1,2,4,5,6-pentamonophosphate 1,3,4,5,6-pentamonophosphate 2,3,4,5,6-pentamonophosphate |
| Example 16F | Pentamonophospho-monopyrophosphate | 1,2,3,4,5-pentamonophosphate-6-pyrophosphate 1,2,3,4,6-pentamonophosphate-5-pyrophosphate 1,2,3,5,6-pentamonophosphate-4-pyrophosphate 1,2,4,5,6-pentamonophosphate-3-pyrophosphate 1,3,4,5,6-pentamonophosphate-2-pyrophosphate 2,3,4,5,6-pentamonophosphate-1-pyrophosphate |
| Example 16G | Tetramonophospho-dipyrophosphate | 1,2,3,4-tetramonophosphate-5,6-dipyrophosphate; 1,2,3,5-tetramonophosphate-4,6-dipyrophosphate; 1,2,3,6-tetramonophosphate-4,5-dipyrophosphate; 1,2,4,5-tetramonophosphate-3,6-dipyrophosphate; 1,2,4,6-tetramonophosphate-3,5-dipyrophosphate; 1,3,4,5-tetramonophosphate-2,6-dipyrophosphate; 1,3,4,6-tetramonophosphate-2,5-dipyrophosphate; 1,3,5,6-tetramonophosphate-2,4-dipyrophosphate; 2,3,4,5-tetramonophosphate-1,6-dipyrophosphate; 2,3,4,6-tetramonophosphate-1,5-dipyrophosphate; 2,4,5,6-tetramonophosphate-1,3-dipyrophosphate; 3,4,5,6-tetramonophosphate-1,2-dipyraphosphate; |
| Example 16H | Trimonophospho-tripyrophosphate | 1,2,3-trimonophosphate-4,5,6-tripyrophosphate; 1,2,4-trimonophosphate-3,5,6-tripyrophosphate; 1,2,5-trimonophosphate-3,4,6-tripyrophosphate; 1,2,6-trimonophosphate-3,4,5-tripyrophosphate; 2,3,4-trimonophosphate-1,5,6-tripyrophosphate; 2,3,5-trimonophosphate-1,4,6-tripyrophosphate; 2,3,6-trimonophosphate-1,4,5-tripyrophosphate; 2,4,5-trimonophosphate-1,3,6-tripyrophosphate; 2,4,6-trimonophosphate-1,3,5-tripyrophosphate; 2,5,6-trimonophosphate-1,3,4-tripyrophosphate; 3,4,5-trimonophosphate-1,2,6-tripyrophosphate; 3,4,6-trimonophosphate-1,2,5-tripyrophosphate; 4,5,6-trimonophosphate-1,2,3-tripyrophosphate |
| Example 16 I | Mono-monophosphate-monopyrophosphate | 1-monophosphate-2-monopyrophosphate; 1-monophosphate-3-monopyrophosphate; 1-monophosphate-4-monopyrophosphate; 1-monophosphate-5-monopyrophosphate; 1-monophosphate-6-monopyrophosphate; 2-monophosphate-1-monopyrophosphate; 2-monophosphate-3-monopyrophosphate; 2-monophosphate-4-monopyrophosphate; 2-monophosphate-5-monopyrophosphate; 2-monophosphate-6-monopyrophosphate; |

| Example | Type of phosphate material | Species of phosphate |
|---|---|---|
| | | 3-monophosphate-1-monopyrophosphate; |
| | | 3-monophosphate-2-monopyrophosphate; |
| | | 3-monophosphate-4-monopyrophosphate; |
| | | 3-monophosphate-5-monopyrophosphate; |
| | | 3-monophosphate-6-monopyrophosphate; |
| | | 4-monophosphate-1-monopyrophosphate; |
| | | 4-monophosphate-2-monopyrophosphate; |
| | | 4-monophosphate-3-monopyrophosphate; |
| | | 4-monophosphate-5-monopyrophosphate; |
| | | 4-monophosphate-6-monopyrophosphate; |
| | | 5-monophosphate-1-monopyrophosphate; |
| | | 5-monophosphate-2-monopyrophosphate; |
| | | 5-monophosphate-3-monopyrophosphate; |
| | | 5-monophosphate-4-monopyrophosphate; |
| | | 5-monophosphate-6-monopyrophosphate; |
| | | 6-monophosphate-1-monopyrophosphate |
| | | 6-monophosphate-2-monopyrophosphate |
| | | 6-monophosphate-3-monopyrophosphate |
| | | 6-monophosphate-4-monopyrophosphate |
| | | 6-monophosphate-5-monopyrophosphate |

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

REFERENCES CITED IN THE ABOVE SPECIFICATION

Ishikawa T, Nakatsuru Y. Zarkovic M, Shamsuddin A M (1999) Inhibition of skin cancer by IP6 in vivo: initiation-promotion model. Anticancer Res 19:3749-3752.

Gupta K P, Singh J. Bharathi R (2003) Suppression of DMBA-induced mouse skin tumor development by inositol hexaphosphate and its mode of action. Nutr Cancer 46:66-72.

Koluppaswamy K, Williams K A, Benaxzi C. Sarli G. McLeod C G Jr. Vucenik I, DeTolla L J (2009) Effect of inositol hexaphosphate on the development of UVB-induced skin tumors in SKH1 hairless mice. Comp Med 59:147-152.

Chen N, Ma W Y, Dong Z (2001) Inositol hexaphosphate inhibits ultraviolet B-induced signal transduction. Mol Carcinog 31:139-144.

Williams K A, Kolappaswamy K, Detolla L J, Vucenik I (2011) Protective effect of inositol hexaphosphate against UVB damage in HaCaT cells and skin carcinogenesis in SKH1 hairless mice. Comp Med 61:39-44.

El-Sherbiny Y M, Cox M C, Ismail Z A, Shamsuddin A M, Vucenik I (2001) G0/G1 arrest and S phase inhibition of human cancer cell lines by inositol hexaphosphate (IP6). Anticancer Res 21:2392-2403.

Estensen R D, Wattenberg L W (1993) Studies of chemo-preventive effects of myo-inositol on benzo[a]pyrene-induced neoplasia of the lung and forestomach of female A/J mice. Carcinogenesis 14:1975-1977.

Gustafson A M, Soldi R, Anderlind C, Scholand M B, Qian J X, Zhang X, Cooper K. Walker D. McWillimas A. Liu G, Szabo E, Brody J, Massion P P, Lenburg M E, Lam S, Bild A H. Spira A (2010) Airway PI3K pathway activation is an early and reversible event in lung cancer development. Sci Transl. Med. 2010, Apr. 7 2:26ra25.

Gu M, Roy S. Raina K, Agarwal C. Agarwal R (2009) Inositol Hexaphosphate Suppresses Growth and Induces Apoptosis in Prostate Carcinoma Cells in Culture and Nude Mouse Xenograft PI3K-Akt Pathway as Potential Target. Cancer Res 69:9465-9472.

Hecht S S, Upadhyaya P, Wang M, Bliss R L, McIntee E J, Kenney P M (2002) Inhibition of lung tumorigenesis in A/J mice by N-acetyl-S—(N-2-phenethylthiocarbamoyl)-L-cysteine and myo-inositol, individually and in combination. Carcinogenesis 23:1455-1461.

Huang C, Ma W Y, Hecht S S, Doug Z (1997) Inositol hexaphosphate inhibits cell transformation and activator protein I activation by targeting phosphatidylinositol-3' kinase. Cancer Res 57:2873-2878.

Lam S, McWilliams A, LeRiche J, MacAulay C. Wattenberg L, Szabo E. (2006) A phase I study of myo-inositol for lung cancer chemoprevention. Cancer Epidemiol. Biomarkers Prev. 15:1526-1531.

Lee H J, Lee S A, Choi H (2005) Dietary administration of inositol and/or inositol-6-phosphate prevents chemically-induced rat hepatocarcinogenesis. Asian Pac J Cancer Prev 6:41-47.

Sakamoto K, Venkatrman G, Shamsuddin A M (1993) Growth inhibition and differentiation of HT-29 cells in vitro by inositol hexaphosphate (phytic acid). Carcinogenesis 14:1815-1819.

Schröterová L, Hasková P, Rudolf E, Cervinka M (2010) Effect of phytic acid and inositol on the proliferation and apoptosis of cells derived from colorectal carcinoma. Oncol Rep 23:787-793.

Shamsuddin A M, Elsayed A M, Ullah A (1988), Suppression of large intestinal cancer in F344 rats by inositol hexaphosphate. Carcinogenesis 9:577-580.

Shamsuddin A M, Ullath A, Chakravarthy A K (1989) Inositol and inositol hexaphosphate suppress cell proliferation and tumor formation in CD-1 mice. Carcinogenesis 10(8):1461-3.

Tian Y, Song Y (2006) Effects of inositol hexaphosphate on proliferation of HT-29 human colon carcinoma cell line. World J Gastroenterol 14:4137-4142.

Norzulina S, Norhaizan M E, Hairuszah I, Norashareena M S (2010) Anticarcinogenic efficacy of phytic acid extracted from rice bran on azoxymethane-induced colon carcinogenesis in rats. *Exp Toxicol Pathol* 62:259-268.

Ullah A, Shamsuddin A M (1990) Dose-dependent inhibition of large intestinal cancer by inositol hexaphosphate in F344 rats. *Carcinogenesis* 11:2219-22.

Witschi H, Espiritu 1, Uveminami D (1999) Chemoprevention of tobacco smoke-induced lung tumors in A/J strain mice with dietary myo-inositol and dexamethasone. *Carcinogenesis* 20:1375-1378.

ARNOLD et al: Evaluation of Chemoprotective Agents in Different Mechanistic Classes Using a Rat Tracheal Epithelial Cell Culture Transformation Assay; Cancer Res. 1995, 55:537-543

FERRY et al; Inositol hexaksiphosphate blocks tumor cell growth by activating apoptic machinery as well as inhibiting the Akt/NFkB mediated cell survival patway; Carcinogenesis 2002, Vol 23, No 12 2031-2041

HUANG et al; Inositol Hexaphosphate Inhibits Cell Transformation and Activator Protein I Activation by Targeting Phosphatidylinositol-3' Kinase, Cancer Res. 1997; 57, 2873-2878

NURUL-HUSNA, et a; Rice bran phytic acid (IP6) induces growth inhibition, cell cycle arrest and apaptosis on human colorectal adenocarcinoma cells. Journal of Medicicnal Plants Research, 2010 Nov. 4, Vol 4(21) 2283-2289

SAKAMOTO, et al; Growth inhibition and differentiation of HT-29 cells in vitro by inositol hexaphosphate (phytic acid), Carcinogenesis, 1993, Vol 14, No 9, 1815-1819

SHAMSUDDIN, et al; Inositol hexaphosphate inhibits growth and induces differentiation of PC-3 human prostate cancer cells, Carcinogenesis, 1995, Vol 16, No 8, 1975-1979

SINGH, et al; Inositol hexaphosphate inhibits growth and induces GI arrest and apoptotic death of prostate carcinoma DU145 cells: modulation of CDK1-CDK-cyclin and pRb-related protein-E2F complexes. Carcinogenesis, 2003, Vol 24, No 3, 555-563

VUCENIK, et al; Cancer Inhibition by Inositol Hexaphosphate (IP6) and Inositol: From Laboratory to Clinic, American Society for Nutritional Sciences, 2003, 3778S-3784S Z I, et al; Impairment of erbB1 receptor and fluid-phase endocytosis and associated mitogenic signaling by inositol hexaphosphate in human prostate carcinoma DU145 cells. Carcinogenesis, 2000, Vol 21, No 12, 2225-2235

BABICH, et al; Comparative cytotoxicities of selected minor dietary non-nutrients with chemopreventive properties. Cancer Lett. 1993 Sep. 30; 73(2-3):127-33

DELILIERS, et al; Effect of inositol hexaphosphate (IP(6)) on human normal and leukaemic haematopoietic cells. Br J Haematol. 2002 June; 117(3):577-87

IUORNO, et al; Effects of d-chiro-inositol in lean women with the polycystic ovary syndrome, Endocr Pract. 2002 November-December; 8(6):417-23

JENAB, et al; Phytic acid in wheat bran affects colon morphology, cell differentiation and apoptosis; Carcinogenesis (2000) 21 (8): 1547-1552

NESTLER, et al; Ovulatory and metabolic effects of D-chiro-inositol in the polycystic ovary syndrome, N Engl J Med. 1999 Apr. 29; 340(17):1314-20

NICKEL, et al; Inositol hexaphosphate reduces 12-O-tetradecanoylphorbol-13-acetate-induced ornithine decarboxylase independent of protein kinase C isoform expression in keratinocytes; Cancer Lett. 1999 Jun. 1; 140(1-2):105-11

RIZVI, et al; Inositol hexaphosphate (IP6) inhibits cellular proliferation in melanoma; J Surg Res. 2006 Jun. 1; 133(1):3-6. Epub 2006 Mar. 23

SHAMSUDDIN A M, BATEN A, LALWANI N D; Effects of inositol hexaphosphate on growth and differentiation in K-562 erythroleukemia cell line; Cancer Lett. 1992 Jul. 10; 64(3):195-202

SHAMSUDDIN A M, YANG G Y, VUCENIK I.; Novel anti-cancer functions of IP6: growth inhibition and differentiation of human mammary cancer cell lines in vitro: Anticancer Res. 1996 November-December; 16(6A): 3287-92

YANG G Y, SHAMSUDDIN A M.; IP6-induced growth inhibition and differentiation of IT-29 human colon cancer cells: involvement of intracellular inositol phosphates; Anticancer Res. 1995 November-December; 15(6B): 2479-97

VUCENIK I, KALEBIC T, TANTIVEJKUL K, SHAMSUDDIN A M.; Novel anticancer function of inositol hexaphosphate: inhibition of human rhabdomyosamoma in vitro and in vivo; Anticancer Res. 1998 May-June; 18(3A):1377-84

VUCENIK I, TANTIVEJKUL K, ZHANG Z S, COLE K E, SAIED I, SHAMSUDDIN A M; IP6 in treatment of liver cancer. 1. IP6 inhibits growth and reverses transformed phenotype in HepG2 human liver cancer cell line; Anticancer Res. 1998 November-December; 18(6A):4083-90

YANG G Y, SHAMSUDDIN A M; IP6-induced growth inhibition and differentiation of HT-29 human colon cancer cells: involvement of intracellular inositol phosphates: Anticancer Res. 1995 November-December; 15(6B): 2479-87

ORAZALINA S, NORHAIZAN M E, HAIRUSZAH I, NORASHAREENA MS. Anticarcinogenic efficacy of phytic acid extracted from rice bran on azoxymethane-induced colon carcinogenesis in rats. Exp Toxicol Pathol 2010; 62:259-268.

I claim:

1. An aqueous liquid formulation, comprising:
   (a) water;
   (b) at least one phosphorylated inositol isomer selected from myoinositol hexaphosphate or an orally-acceptable salt thereof, at a concentration of about 0.5 to about 4% (w/v);
   (c) N-Acetyl-L-cysteine;
   (d) about 0.025 to about 0.05% (w/v) L-Ascorbic acid or L-Ascorbate;
   (e) Genistein; and
   (f) a liposomal-encapsulated Ubiquinol, wherein the ratio of the liposomal-encapsulated ubiquinol to the myoinositol hexaphosphate or the orally-acceptable salt thereof is 1:2.5 to 1:25 (w/v).

2. The formulation of claim 1, further comprising at least one unphosphorylated inositol or optical isomer thereof, present in the form as the inositol isomer in the phosphorylated inositol isomer.

3. The formulation of claim 1, further comprising at least one unphosphorylated inositol or optical isomer thereof, present in a different inositol isomeric form from that of the phosphorylated inositol isomer.

4. The formulation of claim 1, further comprising Luteolin.

5. The formulation of claim 1, further comprising Resveratrol.

6. The formulation of claim 1, further comprising Catechin.

7. The formulation of claim 6, wherein the Catechin is (—)-Catechin gallate.

8. The formulation of claim 1, further comprising Rutin.

9. The formulation of claim 8, wherein the Rutin is Rutin hydrate.

10. The formulation of claim 1, wherein the myoinositol hexaphosphate is present in the formulation at about 0.5 to about 4% (w/v).

11. The formulation of claim 1, wherein the molar ratio of myoinositol hexaphosphate to unphosphorylated myoinositol is about 6:1 to 1:6.

12. The formulation of claim 1, wherein the molar ratio of myoinositol hexaphosphate to unphosphorylated myoinositol is about 1:1.

13. The formulation of claim 1, wherein the L-Ascorbic acid is present in the formulation in an amount of about 22.5 to about 90 mg.

14. The formulation of claim 1, wherein the Genistein is present in the formulation in an amount of about 1 to about 5 mg.

15. The formulation of claim 1, further comprising Vitamin B12.

16. The formulation of claim 1, further comprising Vitamin B12 in an amount of 0.12 to 0.48 µg (w/v).

17. The formulation of claim 1, wherein the formulation is a liquid nutritional supplement formulated for oral delivery.

18. An aqueous liquid formulation, comprising:
(a) water;
(b) at least one phosphorylated inositol isomer selected from myoinositol hexaphosphate or an orally-acceptable salt thereof, at a concentration of 0.5 to 4% (w/v);
(c) N-Acetyl-L-cysteine;
(d) 0.025 to 0.05% (w/v) L-Ascorbic acid or L-Ascorbate;
(e) Genistein; and
(f) a liposomal-encapsulated Ubiquinol, wherein the ratio of the liposomal-encapsulated ubiquinol to the myoinositol hexaphosphate or the orally-acceptable salt thereof is 1:2.5 to 1:25 (w/v).

* * * * *